(12) United States Patent
Vedananda

(10) Patent No.: US 7,538,135 B2
(45) Date of Patent: May 26, 2009

(54) BENZENESULFONYLAMINO COMPOUNDS AND PHARMACEUTICAL COMPOSITIONS CONTAINING THESE COMPOUNDS

(75) Inventor: Thalaththani Ralalage Vedananda, Shrewsbury, MA (US)

(73) Assignee: Novartis AG, Basel (CH)

(*) Notice: Subject to any disclaimer, the term of this patent is extended or adjusted under 35 U.S.C. 154(b) by 242 days.

(21) Appl. No.: 10/563,708

(22) PCT Filed: Jul. 7, 2004

(86) PCT No.: PCT/EP2004/007442

§ 371 (c)(1),
(2), (4) Date: Jun. 19, 2006

(87) PCT Pub. No.: WO2005/005421

PCT Pub. Date: Jan. 20, 2005

(65) Prior Publication Data
US 2007/0043020 A1    Feb. 22, 2007

Related U.S. Application Data

(60) Provisional application No. 60/485,870, filed on Jul. 8, 2003.

(51) Int. Cl.
A61K 31/553    (2006.01)
A61K 31/415    (2006.01)
A01N 43/56    (2006.01)

(52) U.S. Cl. .............. 514/407; 514/409; 514/406; 548/371.4; 548/372.5

(58) Field of Classification Search .............. 514/407
See application file for complete search history.

(56) References Cited

FOREIGN PATENT DOCUMENTS

| WO | WO 99/38845 | 8/1999 |
| WO | WO 00/47209 | 8/2000 |
| WO | WO 00/64888 | 11/2000 |
| WO | WO 00/78312 | 12/2000 |
| WO | WO 01/00579 | 1/2001 |
| WO | WO 01/82916 | 11/2001 |
| WO | WO 02/060388 | 8/2002 |
| WO | WO 02/096358 | 12/2002 |

OTHER PUBLICATIONS

Bergeim et al., J. Am. Chem. Soc. (1944), 66, p. 1459-1460.*
Vidyasagar, A. et al. Journal of the Indian Chemical Society (1991); 68(10):576-578.*
Wolff, M.E. Burger's Medicinal Chemistry, 5th Ed., Partl, John Wiley & Sons, 1995, p. 975-977.*
Banker et al., Modern Pharmaceutics, 3th Ed., Marcel Dekker, New York, 1996, p. 451 and 596.*
Malamas et al., "New Azolidinediones as Inhibitors of Protein Tyrosine Phosphatase 1 B with Antihyperglycemic Properties"< J Med Chem. vol. 43, No. 5, pp. 995-1010 (2000).

* cited by examiner

Primary Examiner—Kamal A Saeed
Assistant Examiner—Valerie Rodriguez-Garcia
(74) Attorney, Agent, or Firm—Mark Milstead

(57) ABSTRACT

Compounds of the formula

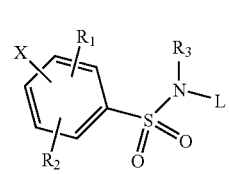

(I)

provide pharmacological agents which bind to Peroxisome Proliferator-Activated Receptors (PPARs). Accordingly, the compounds of the instant invention are useful for the treatment of conditions mediated by the PPAR receptor activity in mammals. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases (IBDs), ulcerative colitis and Crohn's disease, and conditions in which impaired glucose tolerance, hyperglycemia and insulin resistance are implicated, such as type-1 and type-2 diabetes, and Syndrome X.

10 Claims, No Drawings

BENZENESULFONYLAMINO COMPOUNDS AND PHARMACEUTICAL COMPOSITIONS CONTAINING THESE COMPOUNDS

The present invention provides compounds of the formula

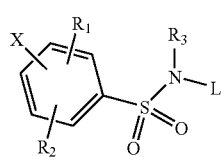

(I)

wherein
$R_1$ and $R_2$ are independently hydrogen, halogen, hydroxy, optionally substituted alkyl, alkoxy, alkylthio, aralkyl or heteroaralkyl; or
$R_1$ and $R_2$ combined together with the carbon atoms to which they are attached form an optionally substituted fused 5- to 6-membered aromatic or heteroaromatic ring provided that $R_1$ and $R_2$ are attached to carbon atoms adjacent to each other; or
$R_1$ and $R_2$ combined are alkylene which together with the carbon atoms to which they are attached form a fused 5- to 7-membered ring provided that $R_1$ and $R_2$ are attached to carbon atoms adjacent to each other; or
$R_1$—C and $R_2$—C may independently be replaced by nitrogen;
$R_3$ is hydrogen or optionally substituted lower alkyl;
X is -Z-$(CH_2)_p$-Q-W wherein
  Z is a bond, O, S, S(O), S(O)$_2$ or —C(O)—; or
  Z is —C(O)NR$_4$— in which
    $R_4$ is hydrogen, alkyl or aralkyl;
  p is an integer from 1 to 8;
  Q is a bond; or
  Q is —O(CH$_2$)$_r$— or —S(CH$_2$)$_r$— in which
    r is zero or an integer from 1 to 8; or
  Q is —C(O)— or —C(O)NR$_5$— in which
    $R_5$ is hydrogen, optionally substituted alkyl, cycloalkyl, aryl, heteroaryl, aralkyl or heteroaralkyl; or
  Q is —NR$_6$—, —NR$_6$C(O)—, —NR$_6$C(O)NR$_7$— or —NR$_6$C(O)O— in which
    $R_6$ is hydrogen, optionally substituted alkyl, cycloalkyl, aryl, heteroaryl, aralkyl or heteroaralkyl;
    $R_7$ is hydrogen, alkyl or aralkyl;
  W is cycloalkyl, aryl, heterocyclyl, aralkyl or heteroaralkyl; or
  W and $R_5$ taken together with the nitrogen atom to which they are attached form a 3- to 7-membered monocyclic or 8- to 12-membered bicyclic ring, which may be optionally substituted or may contain another heteroatom selected from oxygen, nitrogen and sulfur, or
  W and $R_7$ taken together with the nitrogen atom to which they are attached form a 3- to 7-membered monocyclic or 8 to 12-membered bicyclic ring, which may be optionally substituted or may contain another heteroatom selected from oxygen, nitrogen and sulfur;
L is a 5-membered aromatic heterocycle attached through a carbon atom;

or a pharmaceutically acceptable salt thereof; or a prodrug derivative thereof.

The compounds of the present invention provide pharmacological agents which bind to Peroxisome Proliferator-Activated Receptors (PPARs). Accordingly, the compounds of the instant invention are useful for the treatment of conditions mediated by the PPAR receptor activity in mammals. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases (IBDs), ulcerative colitis and Crohn's disease. The compounds of the present invention are particularly useful in mammals as hypoglycemic agents for the treatment and prevention of conditions in which impaired glucose tolerance, hyperglycemia and insulin resistance are implicated, such as type-1 and type-2 diabetes, and Syndrome A.

Listed below are definitions of various terms used to describe the compounds of the instant invention. These definitions apply to the terms as they are used throughout the specification unless they are otherwise limited in specific instances either individually or as part of a larger group, e.g., wherein an attachment point of a certain group is limited to a specific atom within that group, the point of attachment is defined by an arrow at the specific atom.

The term "optionally substituted alkyl" refers to unsubstituted or substituted straight or branched chain hydrocarbon groups having 1 to 20 carbon atoms, preferably 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkanoyl, alkoxy, alkyloxyalkoxy, alkanoyloxy, amino, alkylamino, dialkylamino, alkanoylamino, thiol, alkylthio, alkylthiono, alkylsulfonyl, arylsulfonyl, heteroarylsulfonyl, sulfonamido, nitro, cyano, carboxy, alkoxycarbonyl, aryl, alkenyl, alkynyl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those alkyl groups as described above having 1 to 4 carbon atoms.

The term "halogen", "halide" or "halo" refers to fluorine, chlorine, bromine and iodine.

The term "alkenyl" refers to any of the above alkyl groups having at least two carbon atoms and further containing a carbon to carbon double bond at the point of attachment. Groups having 2 to 4 carbon atoms are preferred.

The term "alkynyl" refers to any of the above alkyl groups having at least two carbon atoms and further containing a carbon to carbon triple bond at the point of attachment. Groups having 2 to 4 carbon atoms are preferred.

The term "alkylene" refers to a straight chain bridge of 1 to 6 carbon atoms connected by single bonds (e.g., —(CH$_2$)$_x$— wherein x is 1 to 6), which may be interrupted with one or more heteroatoms selected from oxygen, sulfur and nitrogen, and may be substituted with 1 to 3 substituents such as alkyl, alkoxy, halo, hydroxy, cycloalkyl, alkanoyl, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "cycloalkyl" refers to optionally substituted monocyclic, bicyclic or tricyclic hydrocarbon groups of 3 to 12 carbon atoms, each of which may optionally be substituted by one or more substituents, such as alkyl, halo, oxo, hydroxy, alkoxy, alkanoyl, amino, alkylamino, dialkylamino, thiol, alkylthio, nitro, cyano, carboxy, carboxyalkyl, alkoxycarbonyl, alkyl- and arylsulfonyl, sulfonamido, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.

The term "acyl" refers to alkanoyl, aroyl, heteroaroyl, arylalkanoyl or heteroarylalkanoyl.

The term "alkanoyl" refers to alkyl-C(O)—.

The term "alkanoyloxy" refers to alkyl-C(O)—O—.

The terms "alkylamino" and "dialkylamino" refer to alkyl-NH— and (alkyl)$_2$N—, respectively.

The term "alkanoylamino" refers to alkyl-C(O)—NH—.

The term "alkylthio" refers to alkyl-S—.

The term "alkylaminothiocarbonyl" refers to alkyl-NHC(S)—.

The term "trialkylsilyl" refers to (alkyl)$_3$Si—.

The term "trialkylsilyloxy" refers to (alkyl)$_3$SiO—.

The term "alkylthiono" refers to allyl-S(O)—.

The term "alkylsulfonyl" refers to alkyl-S(O)$_2$—.

The term "alkoxycarbonyl" refers to alkyl-O—C(O)—.

The term "alkoxycarbonyloxy" refers to alkyl-O—C(O)O—.

The term "carbamoyl" refers to alkyl-NHC(O)—, (alkyl)$_2$NC(O)—, aryl-NHC(O), alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to four substituents, such as alkyl, halo, hydroxy, alkoxy, alkanoyl, alkanoyloxy, optionally substituted amino, thiol, alkylthio, nitro, cyano, carboxy, carboxyalkyl, alkoxycarbonyl, alkylthiono, alkyl- and arylsulfonyl, sulfonamido, heterocycloyl and the like.

The term "monocyclic aryl" refers to optionally substituted phenyl as described under aryl.

The term "aralkyl" refers to an aryl group bonded directly through an alkyl group, such as benzyl.

The term "aralkylthio" refers to aralkyl-S—.

The term "aralkoxy" refers to an aryl group bonded directly through an alkoxy group.

The term "arylsulfonyl" refers to aryl-S(O)$_2$—.

The term "arylthio" refers to aryl-S—.

The term "aroyl" refers to aryl-C(O)—.

The term "aroylamino" refers to aryl-C(O)—NH—.

The term "aryloxycarbonyl" refers to aryl-O—C(O)—.

The term "heterocyclyl" or "heterocyclo" refers to an optionally substituted, fully saturated or unsaturated, aromatic or non-aromatic cyclic group, for example, which is a 3- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, triazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents selected from the group consisting of:

(a) alkyl;
(b) hydroxy (or protected hydroxy);
(c) halo;
(d) oxo (i.e. =O);
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) nitro;
(l) cyano;
(m) sulfonamido, sulfonamidoalkyl, sulfonamidoaryl or sulfonamidodialkyl;
(n) alkylcarbonyloxy;
(o) arylcarbonyloxy;
(p) arylthio;
(q) aryloxy;
(r) alkylthio;
(s) carbamoyl; and
(t) aryl optionally substituted with alkyl, cycloalkyl, alkoxy, hydroxy, amino, alkylamino, dialkylamino or halo.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like; optionally substituted by, e.g., lower alkyl, lower alkoxy or halo.

The term "heteroarylsulfonyl" refers to heteroaryl-S(O)$_2$—.

The term "heteroaroyl" refers to heteroaroyl-C(O)—.

The term "heteroaralkyl" refer to a heteroaryl group bonded through an alkyl group.

Pharmaceutically acceptable salts of a compound of the present invention refer, in particular, to salts formed with acids, namely acid addition salts, e.g., when a pyrazolyl, an imidazolyl or a triazolyl moiety constitutes part of the structure. The acid addition salts may be formed with mineral acids, organic carboxylic acids or organic sulfonic acids, e.g., hydrochloric acid, maleic acid and methanesulfonic acid, respectively.

Similarly, salts formed with bases, e.g., cationic salts, such as alkali and alkaline earth metal salts, such as sodium, lithium, potassium, calcium, magnesium, as well as ammonium salts, such as ammonium, trimethylammonium, diethylammonium, and tris(hydroxymethyl)-methylammonium salts and salts with amino acids, are possible if an acidic group constitutes part of the structure.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono or disubstituted lower alkyl esters such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester, and the like conventionally used in the art.

The compounds of the invention depending on the nature of the substituents, may possess one or more asymmetric centers. The resulting diastereoisomers, optical isomers, i.e., enantiomers, and geometric isomers are encompassed by the instant invention.

The present invention provides heterocyclic compounds of formula (I), pharmaceutical compositions containing them, methods for preparing such compounds and methods of treating conditions mediated by the RXR and the PPAR activity by administration of a therapeutically effective amount of a compound of the present invention or a pharmaceutical composition thereof.

Preferred are compounds of the formula (I), wherein
L is a 5-membered aromatic heterocycle selected from:

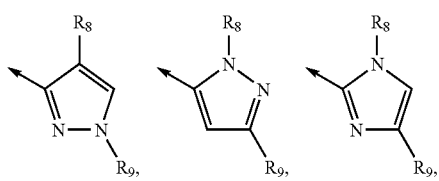

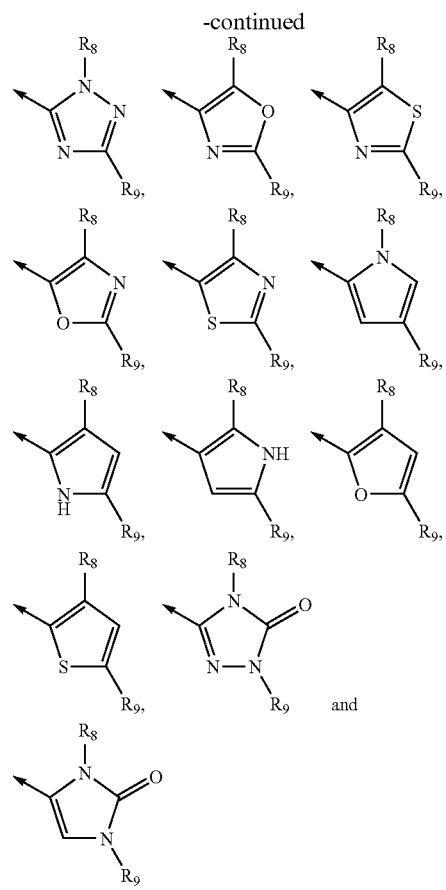

wherein $R_8$ is optionally substituted alkyl, aralkyl, alkoxy, alkylthio, —C(O)$R_{10}$, —C(O)O$R_{11}$ or —C(O)N$R_{12}R_{13}$ in which $R_{10}$ is optionally substituted lower alkyl;

$R_{11}$, $R_{12}$ and $R_{13}$ are independently hydrogen or optionally substituted lower alkyl;

$R_9$ is hydrogen, optionally substituted alkyl, aryl or aralkyl;

or a pharmaceutically acceptable salt thereof; or a prodrug derivative thereof.

Further preferred are compounds of the formula

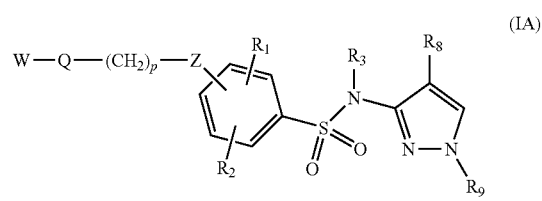

(IA)

wherein $R_1$ and $R_2$ are independently hydrogen, halogen, hydroxy, optionally substituted alkyl, alkoxy, alkylthio, aralkyl or heteroaralkyl; or $R_1$ and $R_2$ combined together with the carbon atoms to which they are attached form an optionally substituted fused 5- to 6-membered aromatic or heteroaromatic ring provided that $R_1$ and $R_2$ are attached to carbon atoms adjacent to each other; or $R_1$ and $R_2$ combined are alkylene which together with the carbon atoms to which they are attached form a fused 5- to 7-membered ring provided that $R_1$ and $R_2$ are attached to carbon atoms adjacent to each other; or $R_1$—C and $R_2$—C may independently be replaced by nitrogen;

$R_3$ is hydrogen or optionally substituted lower alkyl;

Z is a bond, O, S, S(O), S(O)$_2$ or —C(O)—; or

Z is —C(O)NR$_4$— in which
  $R_4$ is hydrogen, alkyl or aralkyl;

p is an integer from 1 to 8;

Q is a bond; or

Q is —O(CH$_2$)$_r$— or —S(CH$_2$)$_r$— in which
  r is zero or an integer from 1 to 8; or Q is —C(O) or —C(O)NR$_5$— in which
  $R_5$ is hydrogen, optionally substituted alkyl, cycloalkyl, aryl, heteroaryl, aralkyl or heteroaralkyl; or Q is —NR$_6$—, —NR$_6$C(O)—, —NR$_6$C(O)NR$_7$— or —NR$_6$C(O)O— in which
  $R_6$ is hydrogen, optionally substituted alkyl, cycloalkyl, aryl, heteroaryl, aralkyl or heteroaralkyl;
  $R_7$ is hydrogen, alkyl or aralkyl;

W is cycloalkyl, aryl, heterocyclyl, aralkyl or heteroaralkyl; or

W and $R_5$ taken together with the nitrogen atom to which they are attached form a 3- to 7-membered monocyclic or 8- to 12-membered bicyclic ring, which may be optionally substituted or may contain another heteroatom selected from oxygen, nitrogen and sulfur; or W and $R_7$ taken together with the nitrogen atom to which they are attached form a 3- to 7-membered monocyclic or 8- to 12-membered bicyclic ring, which may be optionally substituted or may contain another heteroatom selected from oxygen, nitrogen and sulfur;

$R_8$ is optionally substituted alkyl, aralkyl, alkoxy, alkylthio, —C(O)R$_{10}$, —C(O)OR$_{11}$ or —C(O)NR$_{12}$R$_{13}$ in which
  $R_{10}$ is optionally substituted lower alkyl;
  $R_{11}$, $R_{12}$ and $R_{13}$ are independently hydrogen or optionally substituted lower alkyl;

$R_9$ is hydrogen, optionally substituted alkyl, aryl or aralkyl;

or a pharmaceutically acceptable salt thereof; or a prodrug derivative thereof.

Preferred are the compounds of formula (IA) having the formula

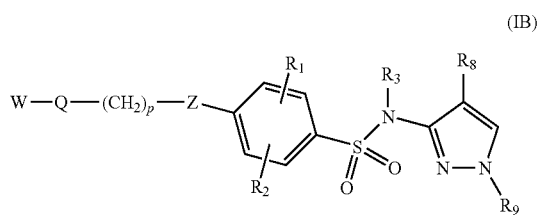

(IB)

wherein
  $R_1$ and $R_2$ are independently hydrogen, halogen, hydroxy, optionally substituted alkyl, alkoxy, alkylthio, aralkyl or heteroaralkyl;
  $R_3$ is hydrogen;
  Z is a bond, O, S, S(O), S(O)$_2$ or —C(O)—; or
  Z is —C(O)NR$_4$— in which
    $R_4$ is hydrogen, alkyl or aralkyl;
  p is an integer from 1 to 5;
  Q is a bond; or
  Q is —O(CH$_2$)$_r$— or —S(CH$_2$)$_r$— in which
    r is zero; or
  Q is —C(O)— or —C(O)NR$_5$— in which
    $R_5$ is hydrogen, optionally substituted alkyl, cycloalkyl, aryl, heteroaryl, aralkyl or heteroaralkyl; or
  Q is —NR$_6$—, —NR$_6$C(O)—, —NR$_6$C(O)NR$_7$— or —NR$_6$C(O)O— in which
    $R_6$ is hydrogen, optionally substituted alkyl, cycloalkyl, aryl, heteroaryl, aralkyl or heteroaralkyl;
    $R_7$ is hydrogen, alkyl or aralkyl;
  W is cycloalkyl, aryl, heterocyclyl, aralkyl or heteroaralkyl;
  $R_8$ is optionally substituted alkyl, aralkyl, alkoxy, alkylthio, —C(O)R$_{10}$, —C(O)OR$_{11}$ or —C(O)NR$_{12}$R$_{13}$ in which
    $R_{10}$ is optionally substituted lower alkyl;
    $R_{11}$, $R_{12}$ and $R_{13}$ are independently hydrogen or optionally substituted lower alkyl;
  $R_9$ is hydrogen, optionally substituted allyl, aryl or aralkyl;

or a pharmaceutically acceptable salt thereof; or a prodrug derivative thereof.

Preferred are compounds of formula (IB), wherein
  $R_1$ and $R_2$ are hydrogen;

or a pharmaceutically acceptable salt thereof; or a prodrug derivative thereof.

Further preferred are compounds of formula (IB) having the formula

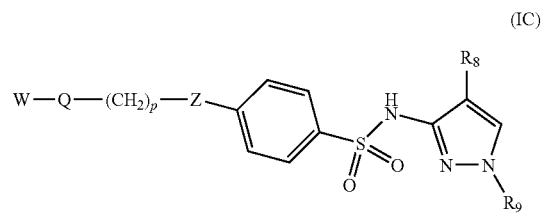

(IC)

wherein
  Z is a bond, O or S;
  p is an integer from 1 to 5;
  Q is a bond; or
  Q is O or S; or
  Q is —C(O)NR$_5$— in which
    $R_5$ is hydrogen, optionally substituted alkyl, cycloalkyl, aryl, heteroaryl, aralkyl or heteroaralkyl; or
  Q is —NR$_6$—, —NR$_6$C(O)—, —NR$_6$C(O)NR$_7$— or —NR$_6$C(O)O— in which
    $R_6$ is hydrogen, optionally substituted alkyl, cycloalkyl, aryl, heteroaryl, aralkyl or heteroaralkyl;
    $R_7$ is hydrogen, alkyl or aralkyl;
  W is cycloalkyl, aryl, heterocyclyl, aralkyl or heteroaralkyl;
  $R_8$ is optionally substituted alkyl, aralkyl, alkoxy, alkylthio, —C(O)R$_{10}$, —C(O)OR$_{11}$ or —C(O)NR$_{12}$R$_{13}$ in which
    $R_{10}$ is optionally substituted lower alkyl;
    $R_{11}$, $R_{12}$ and $R_{13}$ are independently hydrogen or optionally substituted lower alkyl;

$R_9$ is hydrogen, optionally substituted alkyl, aryl or aralkyl;

or a pharmaceutically acceptable salt thereof; or a prodrug derivative thereof.

Preferred are compounds of formula (IC), wherein
$R_8$ is —C(O)OR$_{11}$ in which R$_{11}$ is hydrogen or lower alkyl;
$R_9$ is lower alkyl;

or a pharmaceutically acceptable salt thereof; or a prodrug derivative thereof.

Further preferred are compounds of formula (IC), wherein
$R_8$ is —C(O)OR$_{11}$ in which R$_{11}$ is ethyl;
$R_9$ is ethyl;

or a pharmaceutically acceptable salt thereof; or a prodrug derivative thereof.

Further preferred are also the compounds of formula (IC), designated as the A group, wherein
Z is a bond, O or S;
p is an integer of 2 or 3;
Q is O or S;
W is aryl or heterocyclyl;

or a pharmaceutically acceptable salt thereof; or a prodrug derivative thereof.

Preferred are the compounds in the A group, wherein
W is selected from the group consisting of:

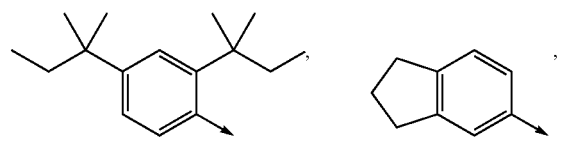

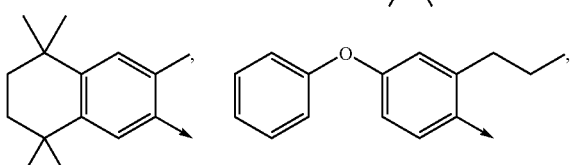

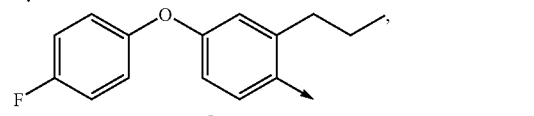

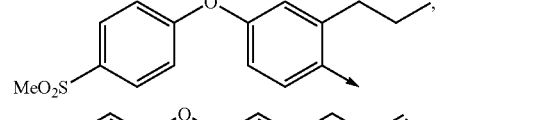

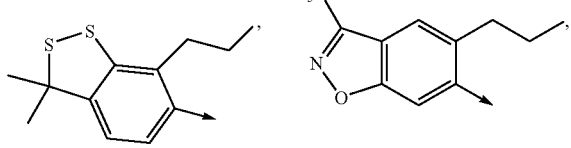

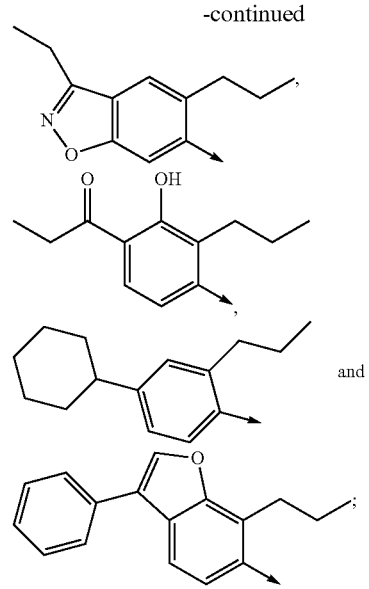

or a pharmaceutically acceptable salt thereof; or a prodrug derivative thereof.

Further preferred are also the compounds of formula (IC), designated as the B group, wherein
Z is O or S;
p is an integer of 1 or 2;
Q is a bond;
W is aryl or heterocyclyl;

or a pharmaceutically acceptable salt thereof; or a prodrug derivative thereof.

Preferred are the compounds in the B group, wherein
W is selected from the group consisting of:

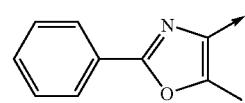

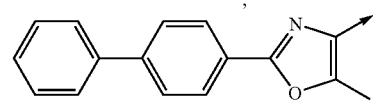

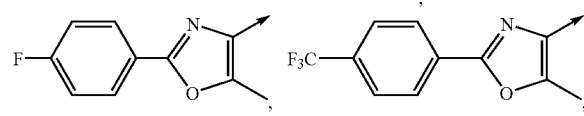

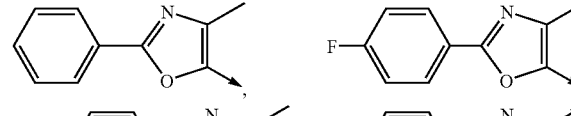

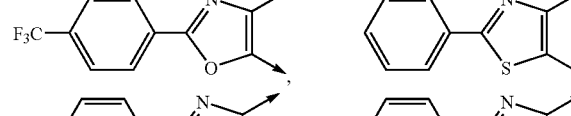

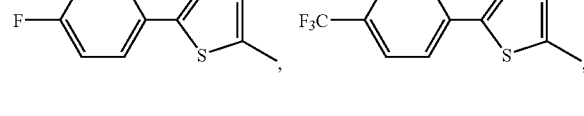

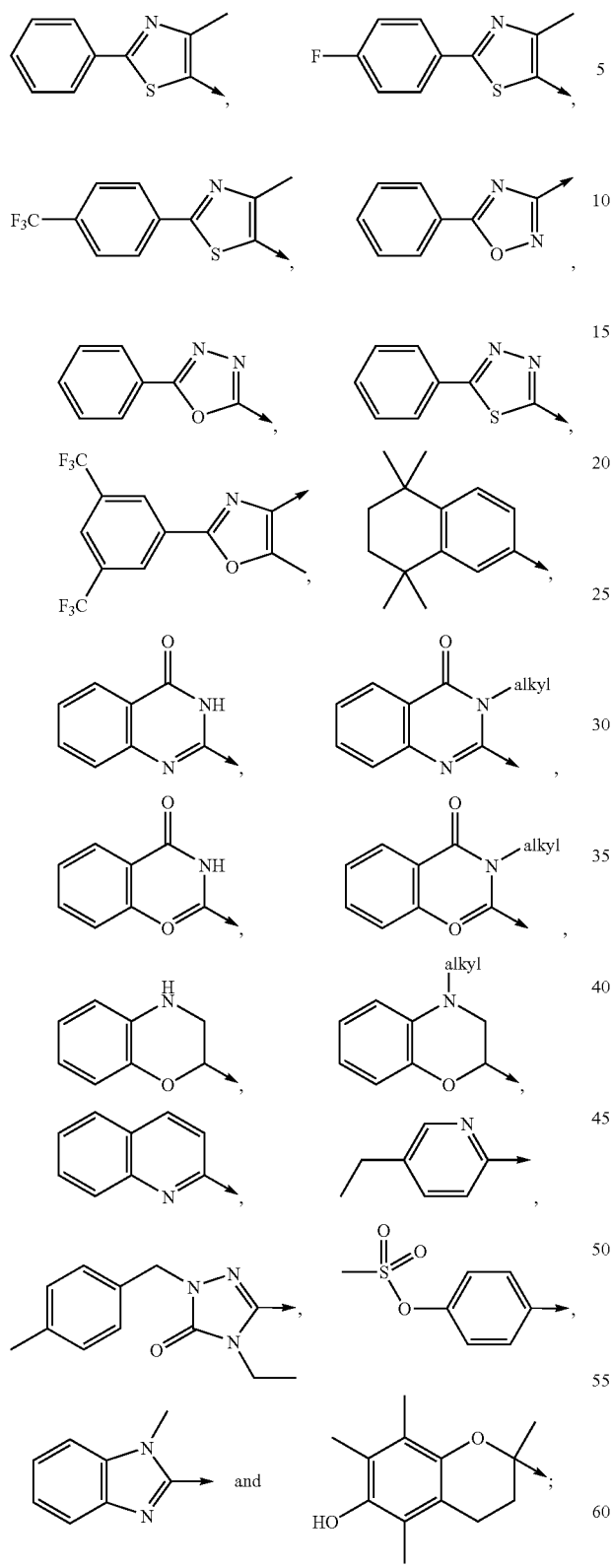

or a pharmaceutically acceptable salt thereof; or a prodrug derivative thereof.

Further preferred are the compounds in the B group, wherein

W is selected from the group consisting of:

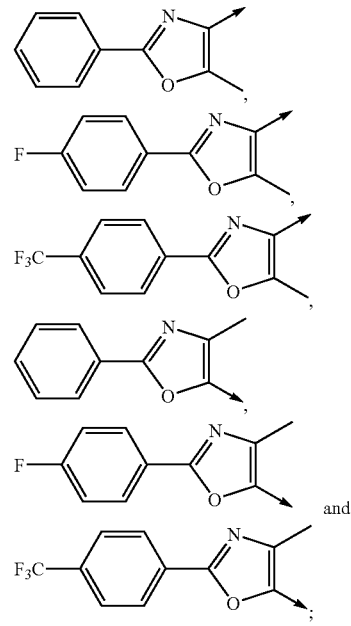

or a pharmaceutically acceptable salt thereof; or a prodrug derivative thereof.

Preferred are also the compounds in the B group, wherein p is 2;

W is selected from the group consisting of:

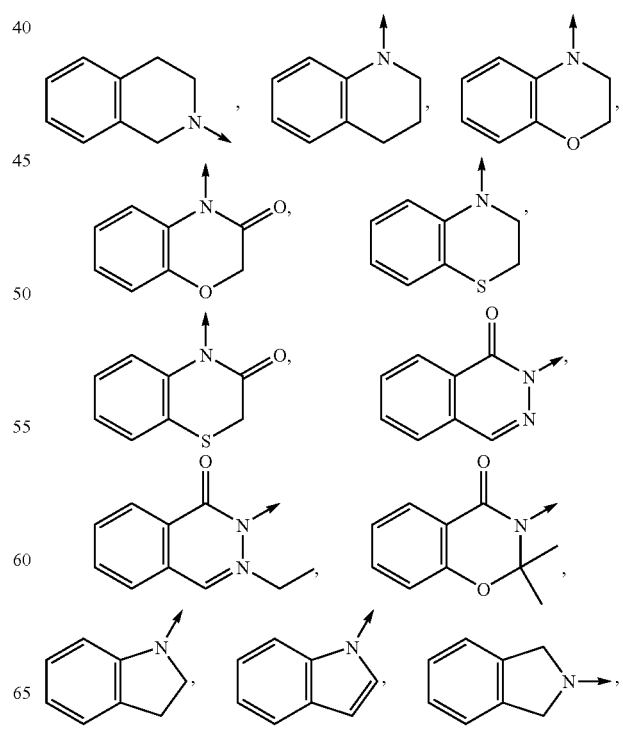

-continued

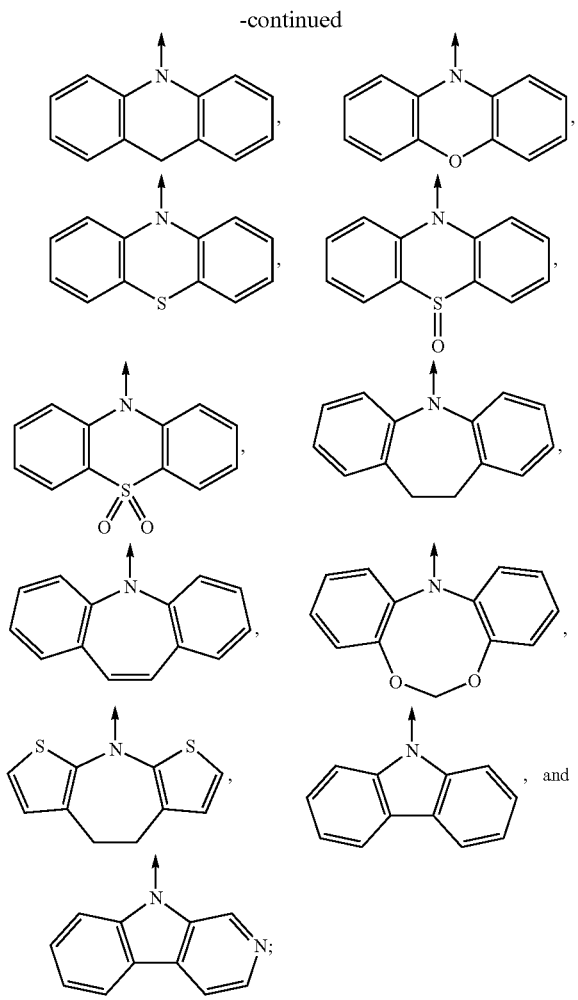

or a pharmaceutically acceptable salt thereof; or a prodrug derivative thereof.

Particular embodiments of the invention are:
3-[4-(5-Methyl-2-phenyl-oxazol-4-ylmethoxy)-benzene-sulfonylamino]-1H-pyrazole-4-carboxylic acid;
1-Benzyl-3-[4-(5-methyl-2-phenyl-oxazol-4-ylmethoxy)-benzenesulfonylamino]-1H-pyrazole-4-carboxylic acid ethyl ester;
1-Benzyl-3-[4-(5-methyl-2-phenyl-oxazol-4-ylmethoxy)-benzenesulfonylamino]-H-pyrazole-4-carboxylic acid;
1-Methyl-3-[4-(5-methyl-2-phenyl-oxazol-4-ylmethoxy)-benzenesulfonylamino]-1H-pyrazole-4-carboxylic acid ethyl ester;
1-Methyl-3-[4-(5-methyl-2-phenyl-oxazol-4-ylmethoxy)-benzenesulfonylamino]-1H-pyrazole-4-carboxylic acid;
1-Ethyl-3-[4-(5-methyl-2-phenyl-oxazol-4-ylmethoxy)-benzenesulfonylamino]-1H-pyrazole-4-carboxylic acid ethyl ester;
1-Ethyl-3-[4-(5-methyl-2-phenyl-oxazol-4-ylmethoxy)-benzenesulfonylamino]-1H-pyrazole-4-carboxylic acid;
1-Allyl-3-[4-(5-methyl-2-phenyl-oxazol-4-ylmethoxy)-benzenesulfonylamino]-1H-pyrazole-4-carboxylic acid ethyl ester;
1-Allyl-3-[4-(5-methyl-2-phenyl-oxazol-4-ylmethoxy)-benzenesulfonylamino]-1H-pyrazole-4-carboxylic acid;
3-{4-[5-Methyl-2-(4-trifluoromethyl-phenyl)-oxazol-4-yl-methoxy]-benzene-sulfonylamino}-1-phenyl-1H-pyrazole-4-carboxylic acid ethyl ester;
3-[4-(5-Methyl-2-phenyl-oxazol-4-ylmethoxy)-benzene-sulfonylamino]-1-propyl-1H-pyrazole-4-carboxylic acid ethyl ester;
1-Ethyl-3-{4-[5-methyl-2-(4-trifluoromethyl-phenyl)-oxazol-4-ylmethoxy]-benzene-sulfonylamino}-1H-pyrazole-4-carboxylic acid ethyl ester;
1-Ethyl-3-[4-(5-methyl-2-phenyl-oxazol-4-ylmethoxy)-benzenesulfonylamino]-1H-pyrazole-4-carboxylic acid methylamide;
1-Ethyl-3-[4-(5-methyl-2-phenyl-oxazol-4-ylmethoxy)-benzenesulfonylamino]-1H-pyrazole-4-carboxylic acid dimethylamide;
1-Ethyl-3-[4-(5-methyl-2-phenyl-oxazol-4-ylmethoxy)-benzenesulfonylamino]-1H-pyrazole-4-carboxylic acid cyclopropylmethyl-amide;
1-Ethyl-3-[4-(5-methyl-2-phenyl-oxazol-4-ylmethoxy)-benzenesulfonylamino]-1H-pyrazole-4-carboxylic acid amide;
1-Ethyl-3-[4-(5-methyl-2-phenyl-oxazol-4-ylmethoxy)-benzenesulfonylamino]-1H-pyrazole-4-carboxylic acid ethylamide;
1-Ethyl-3-[4-(5-methyl-2-phenyl-oxazol-4-ylmethoxy)-benzenesulfonylamino]-H-pyrazole-4-carboxylic acid benzylamide;
N-[1-Ethyl-4-(piperidine-1-carbonyl)-1H-pyrazol-3-yl]-4-(5-methyl-2-phenyl-oxazol-4-ylmethoxy)-benzene-sulfonamide;
N-(4-Benzoyl-1-ethyl-1H-pyrazol-3-yl)-4-(5-methyl-2-phenyl-oxazol-4-ylmethoxy)-benzenesulfonamide; and
1-Ethyl-3-{methyl-[4-(5-methyl-2-phenyl-oxazol-4-yl-methoxy)-benzenesulfonyl]-amino}-1H-pyrazole-4-carboxylic acid ethyl ester;

or a pharmaceutically acceptable salt thereof.

Compounds of formula (I) may be prepared starting from sulfonic acid analogs of the formula

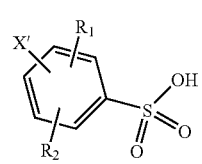

(II)

in which $R_1$ and $R_2$ have meanings as defined herein; X' represents X as defined herein; or X' is a group convertible to X, by treatment with a chlorinating agent, such as thionyl chloride or oxalyl chloride, to form sulfonyl chlorides of the formula

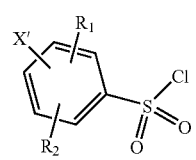

(III)

wherein $R_1$, $R_2$ and X' have meanings as defined for formula (II) using reaction conditions described herein in the Examples, or using conditions well-known in the art.

Sulfonyl chlorides of formula (III) wherein $R_1$, $R_2$ and X' have meanings as defined herein above may then be reacted with an amine of the formula $$R_3'\text{—NH-L'} \qquad (IV),$$

or an acid addition salt thereof, in which $R_3'$ and L' represent $R_3$ and L as defined herein; or $R_3'$ and L' are groups convertible to $R_3$ and L, respectively, in the presence of a base, such as triethylamine (TEA), diisopropylethylamine (DIA), N-methylmorpholine (NMM) or pyridine, to obtain compounds of the formula

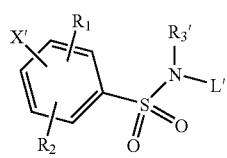

(I')

wherein $R_1$ and $R_2$ have meanings as defined herein above; $R_3'$ and L' have meanings as defined for formula (IV); and X' represents X as defined herein; or X' is a group convertible to X. The reaction may be conducted in the presence of an inert solvent, such as dichloromethane (DCM), N,N-dimethylformamide (DMF) or tetrahydrofuran (THF).

Amines of formula (IV), or acid addition salts thereof, are known or may be prepared according to methods well-known in the art. Preferred are amines of formula (IV) wherein L' is a 5-membered aromatic heterocycle selected from:

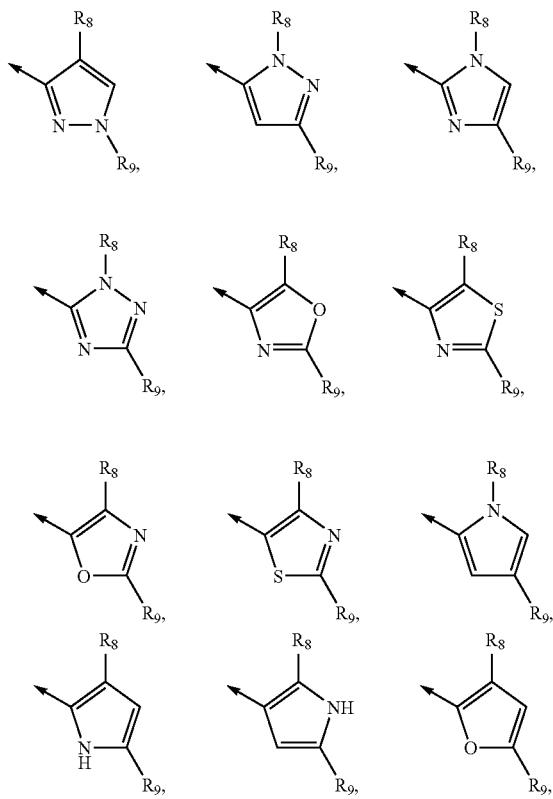

-continued

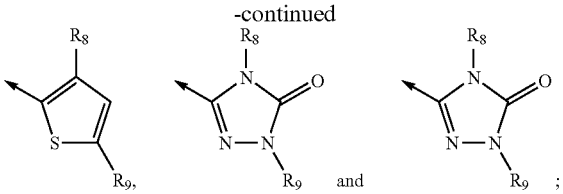

wherein $R_8$ and $R_9$ have meanings as defined herein.

Compounds of formula (I') wherein X' represents X as defined herein may be obtained from compounds of formula (I') wherein X' is a group convertible to X using methods described herein, or modifications thereof, or using methods well-known in the art. For example, compounds of formula (I') in which X' is benzyloxy may first be converted to compounds of the formula

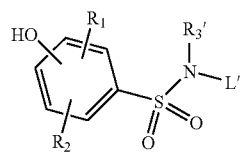

(V)

wherein $R_1$ and $R_2$ have meanings as defined herein above; and $R_3'$ and L' have meanings as defined for formula (IV), e.g., by reduction with hydrogen in the presence of a catalyst, such as palladium on carbon, in a polar organic solvent, such as ethyl acetate (EtOAc) or ethanol (EtOH). The resulting phenols of formula (V) may then be treated with an alkylating agent of the formula $$W\text{-}Q\text{-}(CH_2)_p\text{-Lg} \qquad (VI)$$

wherein p, Q and W have meanings as defined herein; and Lg represents a leaving group, such as iodide, bromide, chloride or trifluoromethanesulfonate, in the presence of a base, such as potassium or cesium carbonate or sodium hydride, and an inert solvent, such as DMF or THF, to form compounds of formula (I') wherein X' is —O—$(CH_2)_p$-Q-W in which p, Q and W have meanings as defined herein above.

Alternatively, compounds of formula (I') wherein X' is —O—$(CH_2)_p$-Q-W in which p, Q and W have meanings as defined herein may be obtained from sulfonic acid analogs of formula (II) in which X' is hydroxy; and $R_1$ and $R_2$ have meanings as defined herein, by converting the compound of formula (II) to its dialkali metal salt, e.g., a disodium salt, using aqueous base, e.g., aqueous sodium hydroxide, in a polar solvent, such as 1,4-dioxane or THF, followed by treatment with an alkylating agent of formula (VIa) wherein p, Q, W and Lg have meanings as defined herein above to afford compounds of the formula

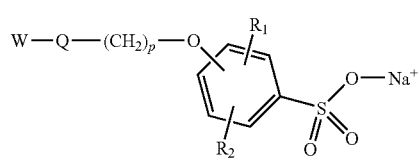

(VII)

wherein $R_1$, $R_2$, p, Q and W have meaning as defined herein.

Compounds of formula (VII) wherein $R_1$, $R_2$, p, Q and W have meaning as defined herein may then be treated with a chlorinating agent, such as thionyl chloride or oxalyl chloride, to afford sulfonyl chlorides of the formula

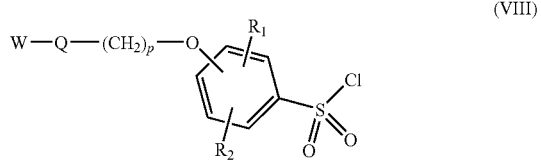
(VIII)

wherein $R_1$, $R_2$, p, Q and W have meaning as defined herein. Sulfonyl chlorides of formula (VIII) may then be reacted with an amine of formula (IV), or an acid addition salt thereof, in which $R_3'$ and L' have meanings as defined herein, in the presence of a base, such TEA, DIA, NMM or pyridine, and an organic solvent, such as DCM or THF, to form compounds of formula (I') in which $R_1$, $R_2$, $R_3'$ and L' have meanings as defined herein; and X' represents —O—$(CH_2)_p$-Q-W in which p, Q and W have meanings as defined herein.

Similarly, compounds of formula (I') wherein $R_1$, $R_2$, $R_3'$ and L' have meanings as defined herein above; and X' is thiol, may be converted to compounds of formula (I') in which X' is —S—$(CH_2)_p$-Q-W. For example, thiophenols of the formula

(IX)

wherein $R_1$ and $R_2$ have meanings as defined herein may be dimerized according to methods well known in the art to form disulfides of the formula

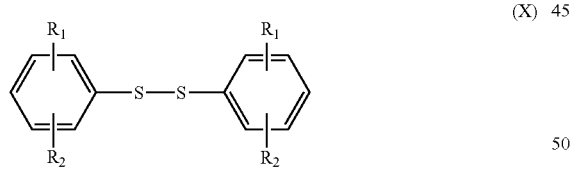
(X)

wherein $R_1$ and $R_2$ have meanings as defined herein.

Compounds of formula (X) wherein $R_1$ and $R_2$ have meanings as defined herein can be converted to bis sulfonyl chlorides of the formula

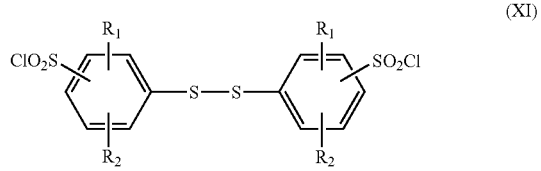
(XI)

wherein $R_1$ and $R_2$ have meanings as defined herein by treatment with chlorosulfonic acid in an inert solvent, such as DCM, followed by basic hydrolysis using, e.g., aqueous sodium hydroxide. The resulting bis sodium salts may then be treated with a chlorinating agent, such as thionyl chloride or oxalyl chloride, to form bis sulfonyl chlorides of formula (XI).

Sulfonyl chlorides of formula (XI) wherein $R_1$ and $R_2$ have meanings as defined herein may be reacted with an amine of the formula

$R_3'$—NH-L'     (IV), or an acid addition salt thereof, in which $R_3'$ and L' represent $R_3$ and L as defined herein; or $R_3'$ and L' are groups convertible to $R_3$ and L, respectively, in the presence of a base, such as TEA, DIEA, NMM or pyridine, and an inert solvent, such as DCM, DMF or THF, to afford disulfides of the formula

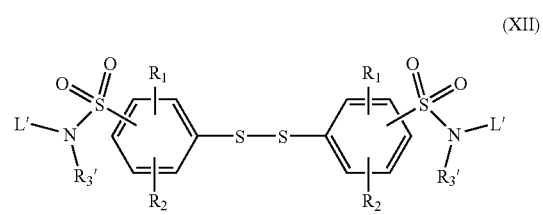
(XII)

wherein $R_1$, $R_2$, $R_3'$ and L' have meanings as defined herein above.

Disulfides of formula (XII) wherein $R_1$ and $R_2$ have meanings as defined herein; and $R_3'$ and L' represent $R_3$ and L as defined herein; or $R_3'$ and L' are groups convertible to $R_3$ and L, respectively, can be reduced to thiols of the formula

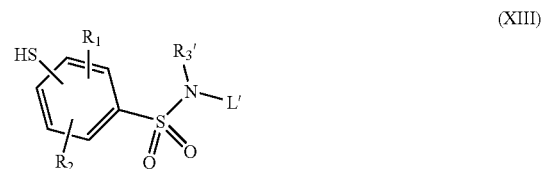
(XIII)

wherein $R_1$, $R_2$, $R_3'$ and L' have meanings as defined herein above by treatment with a reducing agent, such as sodium borohydride or triphenylphosphine, in a polar solvent, such as EtOH or THF, respectively.

Thiols of formula (XIII) may then be treated with an alkylating agent of the formula

W-Q-$(CH_2)_p$-Lg     (VI)

wherein p, Q and W have meanings as defined herein; and Lg represents a leaving group as defined herein above, in the presence of a base, such as potassium or cesium carbonate or sodium hydride, in an inert solvent, such as DMF or THF, to form compounds of formula (I') in which $R_1$, $R_2$, $R_3'$ and L' have meanings as defined herein; and X' represents —S—$(CH_2)_p$-Q-W in which p, Q and W have meanings as defined herein.

Preferably, the allylating agent of formula (VI) is selected from a group wherein p is an integer of 2 or 3; Q is O; Lg is chloride or bromide; and W is or the alkylating agent of formula (VI) is selected from a group wherein p is an integer of 1 or 2; Q is a bond; Lg is chloride or bromide; and W is -continued

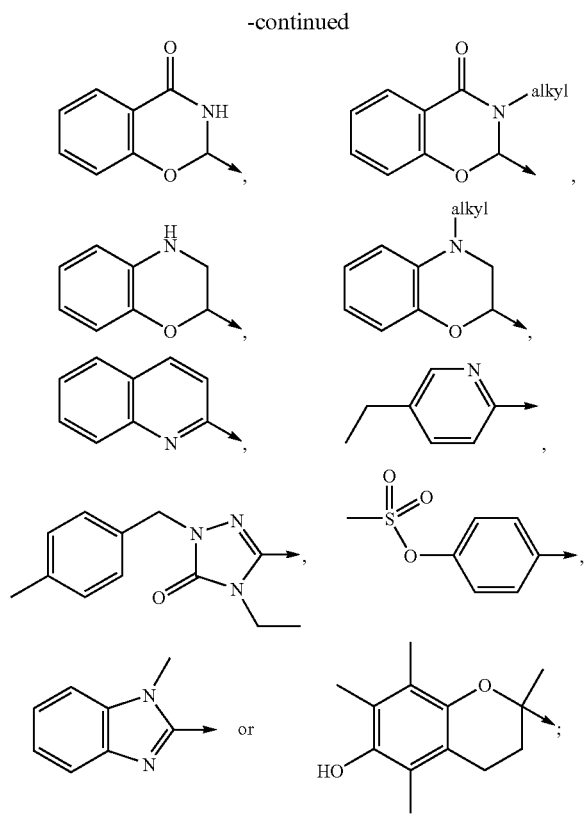

or the alkylating agent of formula (VI) is selected from a group wherein p is 2; Q is a bond; Lg is chloride or bromide; and W is

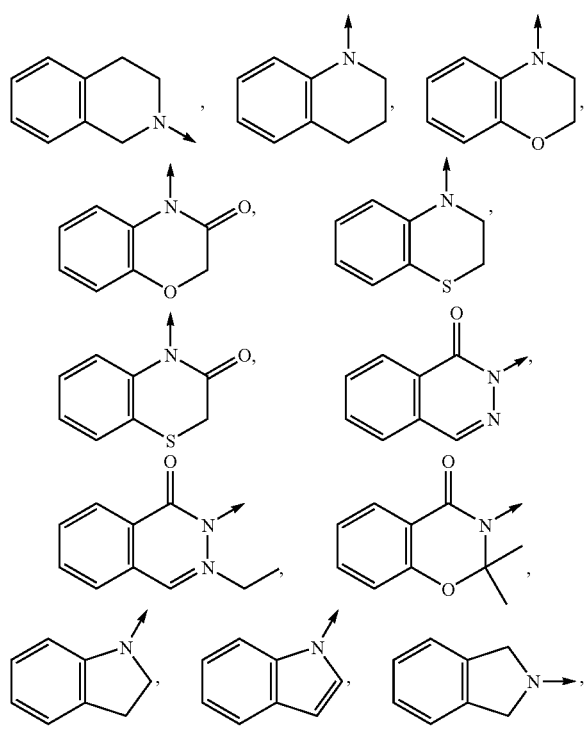

-continued

The alkylating agents of formula (VII) may be prepared using methods described herein, or modifications thereof, or using methods known in the art, e.g., 4-chloromethyl-5-methyl-2-phenyloxazole and 4 may be prepared using methods described in International PCT Patent Application No. WO 00/64888 or according to *J. Med. Chem.*, Vol. 43, pp. 995-1010 (2000). 1-(3-Bromopropoxy)-4-phenoxy-2-propylbenzene may be prepared as described in International PCT Patent Application No. WO 00/78312.

Preferably, alkylating agents of formula (VI) having the formula

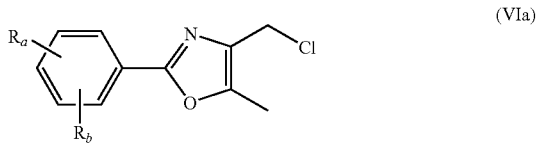

(VIa)

wherein $R_a$ and $R_b$ are independently hydrogen, halogen, alkyl, alkoxy, trifluoromethyl or aryl, may be prepared by treating a compound of the formula

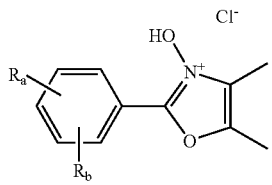
(VIb)

wherein $R_a$ and $R_b$ have meanings as defined for formula (VIa), with a chlorinating agent, such as phosphorus oxychloride ($POCl_3$), in acetonitrile. It is essential that the reaction is carried out in acetonitrile in order to obtain alkylating agents of formula (VIa) in high chemical yield and purity, i.e., the alkylating agents of formula (VIa) are obtained according to the present method in high regioselectivity, preferably in greater than 99% selectivity. The chlorination is preferably conducted at an ambient temperature, more preferably at room temperature.

Compounds of formula (VIb) may be prepared by condensing an aldehyde of the formula

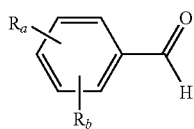
(VIc)

wherein $R_a$ and $R_b$ have meanings as defined for formula (VIb), with 2,3-butadione monooxime of the formula

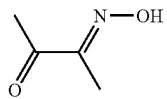
(VId)

in the presence of an acid catalyst such as gaseous hydrochloric acid and an organic solvent, such as ethyl acetate or acetic acid, preferably glacial acetic acid, to afford compounds of formula (VIb) wherein $R_a$ and $R_b$ have meanings as defined herein above.

In a preferred embodiment, the allylating agent of formula (VIa) is 4-chloromethyl-5-methyl-2-[4-(trifluoromethyl)phenyl]-oxazole.

Alternatively, phenols of formula V and thiophenols of formula (XIII) may be reacted with an alcohol of the formula

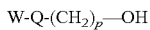
(VI')

wherein p, Q and W have meanings defined herein under Mitsunobu conditions, e.g., in the presence of triphenylphoshine and diethyl azodicarboxylate in an organic solvent, such as THF, to afford compounds of formula (I') in which X' is $-O-(CH_2)_p-Q-W$ or $-S-(CH_2)_p-Q-W$, respectively, and p, Q and W have meanings as defined herein. Alcohols of formula (VI') may be prepared by methods described herein, or modifications thereof, or using methods well-known in the art.

Compounds of formula (I') wherein $R_1$, $R_2$, $R_3'$ and L' have meanings as defined herein; and X' represents $-(CH_2)_p-Q-W$ in which p and W have meanings as defined herein; and Q is O or S, may be obtained by reacting compounds of the formula

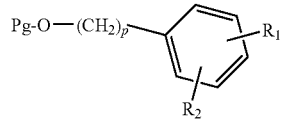
(XIV)

wherein $R_1$, $R_2$ and p have meanings as defined herein above; and Pg represents a protecting group, such as acyl or alkoxycarbonyl, e.g., acetyl, with chlorosulfonic acid in an inert solvent, such as DCM, followed by subsequent treatment with a chlorinating agent, such as thionyl chloride or oxalyl chloride, to afford sulfonyl chlorides of the formula

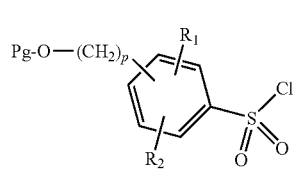
(XV)

wherein $R_1$, $R_2$, p and Pg have meanings as defined for formula (XIV).

Sulfonyl chlorides of formula (XV) may then be condensed with an amine of formula (IV) as described herein above to form compounds of the formula

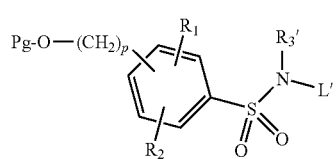
(XVI)

wherein $R_1$, $R_2$, p, Pg, $R_3'$ and L' have meaning as defined herein. Subsequent removal of the protecting group, e.g. when Pg is acetyl the protecting group may be removed in the presence of a base, e.g., aqueous sodium hydroxide, and a polar solvent, such as methanol (MeOH), THF or 1,4-dioxane, affords alcohols of the formula

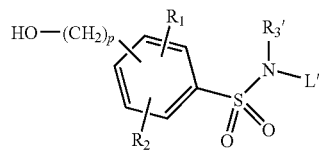
(XVII)

wherein $R_1$, $R_2$, p, $R_3'$ and L' have meaning as defined herein.

Alcohols of formula (XVII) may then be condensed with a compound of formula W—OH or W—SH wherein W represents aryl or heteroaryl, e.g., under Mitsunobu conditions to form compounds of formula (I') wherein $R_1$, $R_2$, $R_3'$ and L' have meanings as defined herein; and X' represents —$(CH_2)_p$-Q-W in which p has meanings as defined herein; W is aryl or heteroaryl; and Q is O or S, respectively.

Alternatively, alcohols of formula (XVII) may also be converted to compounds of the formula

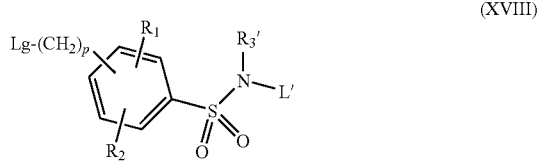

(XVIII)

wherein $R_1$, $R_2$, p, $R_3$' and L' have meaning as defined herein; and Lg represents a leaving as defined herein above, using methods described herein, or modifications thereof, or using methods well-known in the art. Subsequent reaction with alcohols of formula W—OH or thiols of formula W—SH in the presence of a base, such as potassium or cesium carbonate or sodium hydride, in an inert solvent, such as DMF or THF, affords compounds of formula (I') wherein $R_1$, $R_2$, $R_3$' and L' have meanings as defined herein; and X' represents —$(CH_2)_p$-Q-W in which p and W have meanings as defined herein; and Q is O or S, respectively.

Compounds of formula (I') wherein $R_1$, $R_2$, $R_3$' and L' have meanings as defined herein; and X' represents —$C(O)NR_4$—$(CH_2)_p$-Q-W in which $R_4$, p, Q and W have meanings defined herein, may be prepared by reacting an activated derivative of a carboxylic acid of the formula

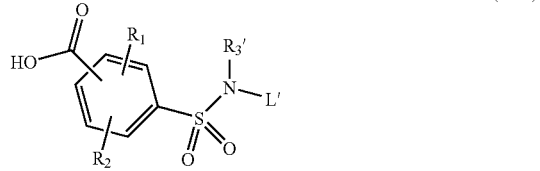

(XIX)

wherein $R_1$, $R_2$, $R_3$' and L' have meanings as defined herein with an amine of the formula

W-Q-$(CH_2)_p$—NH—$R_4$ (XX), or an acid addition salt thereof, wherein $R_4$, p, Q and W have meanings as defined herein.

Carboxylic acids of formula (XIX) and amines of formula (XX) may be prepared using methods described herein, or modifications thereof, or using methods known in the art.

Similarly, compounds of formula (I') wherein $R_1$, $R_2$, $R_3$' and L' have meanings as defined herein; and X' represents -Z-$(CH_2)_p$—$C(O)NR_5$—W in which Z, p, $R_5$ and W have meanings as defined herein, may be prepared by reacting an activated derivative of a carboxylic acid of the formula

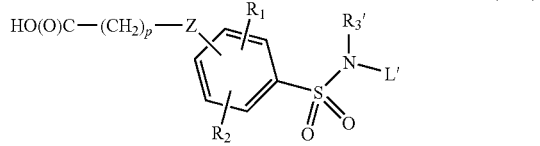

(XXI)

wherein $R_1$, $R_2$, $R_3$', L', Z and p have meanings as defined herein with an amine of the formula

W—NH—$R_5$ (XXII), or an acid addition salt thereof, wherein $R_5$ and W have meanings as defined herein.

Carboxylic acids of formula (XXI) and amines of formula (XXII) may be prepared using methods described herein, or modifications thereof, or using methods known in the art.

In the processes cited herein above, activated derivatives of carboxylic acids, e.g., those corresponding to formula (XIX) and (X)X), include acid chlorides, bromides and fluorides, mixed anhydrides, lower alkyl esters and activated esters thereof, and adducts formed with coupling agents, such as 1-ethyl-3-(3-dimethylaminopropyl)carbodiimide hydrochloride (EDCl), O-(1,2-dihydro-2-oxo-1-pyridyl)-N,N,N',N'-tetramethyluronium tetrafluoroborate and the like. Mixed anhydrides are preferably such from pivalic acid, or lower alkyl hemiesters of carbonic acids, such as ethyl or isobutyl analogs. Activated esters include, for example, succinimido, phthalimido or 4-nitrophenyl esters. The reaction of an activated derivative of a carboxylic acid, e.g., those corresponding to formula (XIX) or (XXI), with an amine, e.g., those of formula (XX) or (XXII), respectively, may be carried out in the presence of a base, such as TEA, DIA or NMM, in an inert solvent, such as DCM, DMF or THF, or a mixture of solvents thereof. Carboxylic acids of formula (XIX) and (XXI) can be converted to their activated derivatives using methods described herein or in the art.

Compounds of formula (I') wherein $R_1$, $R_2$, $R_3$' and L' are as defined herein; and X' represents -Z-$(CH_2)_p$—$NR_6$—W, -Z-$(CH_2)_p$—$NR_6C(O)$—W, -Z-$(CH_2)_p$—$NR_6C(O)NR_7$—W or -Z-$(CH_2)_p$—$NR_6C(O)O$—W in which Z, p, $R_6$, $R_7$ and W have meanings as defined herein, may be obtained by reacting amines of the formula

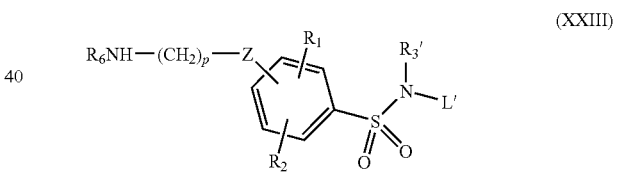

(XXIII)

wherein $R_1$, $R_2$, $R_3$', L', Z, p and $R_6$ have meanings as defined herein with a N-derivatizing agent, such as an activated derivative of a carboxylic acid, an isocyanate, a carbamoyl chloride or a chloroformate, in the presence of a base, such as TEA, DIA or NMM, in an inert solvent, such as DCM, DMF or THF; or amines of formula (XXIII) may be reacted with an aldehyde under conditions of reductive amination. Amines of formula (XXIII) may be prepared using methods described herein, or modifications thereof, or using methods known in the art.

The starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxy groups are those that can be converted under mild conditions into free amino, thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, e.g., in McOmie, "*Protective Groups in Organic Chemistry*", Plenum Press, London, NY (1973); and Greene and Wuts, "*Protective Groups in Organic Synthesis*", John Wiley and Sons, Inc., NY (1999).

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the compounds may be in the form of one of the possible isomers or mixtures thereof, for example, as substantially pure geometric (cis or trans) isomers, optical isomers (antipodes), racemates or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example, by chromatography and/or fractional crystallization.

Any resulting racemates of final products or intermediates can be resolved into the optical antipodes by known methods, e.g., by separation of the diastereoisomeric salts thereof, obtained with an optically active acid or base, and liberating the optically active acidic or basic compound. The carboxylic acid intermediates can thus be resolved into their optical antipodes, e.g., by fractional crystallization of D- or L-(alpha-methylbenzylamine, cinchonidine, cinchonine, quinine, quinidine, ephedrine, dehydroabietylamine, brucine or strychnine)-salts. Racemic products can also be resolved by chiral chromatography, e.g., high pressure liquid chromatography (HPLC) using a chiral adsorbent.

Finally, compounds of the invention are either obtained in the free form, or as a salt thereof if salt forming groups are present.

Acidic compounds of the invention may be converted into salts with pharmaceutically acceptable bases, e.g., an aqueous alkali metal hydroxide, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example, sulfuric acid, a phosphoric or hydrohalic acid; or with organic carboxylic acids, such as ($C_1$-$C_4$)-alkanecarboxylic acids which, for example, are unsubstituted or substituted by halogen, for example, acetic acid, such as saturated or unsaturated dicarboxylic acids, for example, oxalic, succinic, maleic or fumaric acid, such as hydroxy-carboxylic acids, for example, glycolic, lactic, malic, tartaric or citric acid, such as amino acids, for example, aspartic or glutamic acid; or with organic sulfonic acids, such as ($C_1$-$C_4$)-alkyl-sulfonic acids, for example, methanesulfonic acid; or arylsulfonic acids which are unsubstituted or substituted, for example, by halogen. Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

As described herein above, the compounds of the present invention bind to PPARs, and thus may be employed for the treatment of conditions mediated by the PPARs. Such compounds may therefore be employed therapeutically for the treatment of dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by PPAR receptors, in particular, PPARα and PPARγ. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis and Crohn's disease, and conditions in which impaired glucose tolerance, hyperglycemia and insulin resistance are implicated, such as type-1 and type-2 diabetes, and Syndrome X.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with: a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by PPARs, preferably, dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441, NN-57-05445 or RXR ligands such as GW-0791, AGN-194204; sodium-dependent glucose cotransporter inhibitors, such as T-1095; glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimefics; DPPIV (dipeptidyl peptidase IV) inhibitors such as LAF237; hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastabn, squalene synthase inhibitors or FXR (farnesoid X receptor) and LXR (liver X receptor) ligands, cholestyramine, fibrates, nicotinic acid and aspirin; anti-obesity agents, such as orlistat; anti-hypertensive agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na-K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil; aldosterone receptor antagonists and aldosterone synthase inhibitors. Other specific antidiabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents, anti-hypertensive agents or inotropic agents, most preferably from antidiabetics or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by PPARs, preferably, dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

Thus, the present invention also relates to a compound of formula (I) for use as a medicament; to the use of a compound of formula (I) for the preparation of a pharmaceutical composition for the prevention and/or treatment of conditions mediated by PPARs, and to a pharmaceutical composition for use in conditions mediated by PPARs comprising a compound of formula (I), or a pharmaceutically acceptable salt thereof, in association with a pharmaceutically acceptable diluent or carrier therefore.

The present invention further provides a method for the prevention and/or treatment of conditions mediated by PPARs, which comprises administering a therapeutically effective amount of a compound of the present invention.

A unit dosage for a mammal of about 50-70 kg may contain between about 1 mg and 1000 mg, advantageously between about 5-500 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from antidiabetics, hypolipidemic agents, anti-obesity agents, anti-hypertensive agents or inotropic agents. The kit may comprise instructions for its administration.

Similarly, the present invention provides a kit of parts comprising: (i) a pharmaceutical composition of the invention; and (ii) a pharmaceutical composition comprising a compound selected from an antidiabetic, anti-obesity agent, anti-hypertensive agent, inotropic agent or hypolipidemic agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being a antidiabetic, anti-obesity agent, anti-hypertensive agent, inotropic agent or hypolipidemic agent, e.g., as indicated above.

Preferably, a compound of the invention is administered to a mammal in need thereof.

Preferably, a compound of the invention is used for the treatment of a disease which responds to modulation of the PPAR activity, particularly, PPARα and PPARγ activity.

Preferably, the condition associated with PPAR activity is selected from dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

Finally, the present invention provides a method or use which comprises administering a compound of formula (I) in combination with a therapeutically effective amount of an antidiabetic agent, anti-obesity agent, anti-hypertensive agent, inotropic agent or hypolipidemic agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests, using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-5}$ molar and $10^{-10}$ molar concentrations. A therapeutically effective amount in vivo may range depending on the route of administration, between about 1 and 500 mg/kg, preferably between about 5 and 100 mg/kg.

The compounds of the invention bind to the PPARα and PPARγ receptors and, thus, may be employed as agonists and/or antagonists of the PPARα and the PPARγ receptors in mammals.

The activity of a compound according to the invention can be assessed by the following methods or methods well-described in the art:

The in vitro functional binding to the PPARα, PPARδ and PPARγ receptors is determined as follows:

The functional binding assays for the PPARα, PPARδ and PPARγ receptors are a variation of the coactivator-dependent receptor ligand assay (CARLA) (see Krey et al., "Fatty Acids, Eicosanoids, and Hypolipidemic Agents Identified as Ligands of Peroxisome Proliferator-Activated Receptors by Coactivator-Dependent Receptor Ligand Assay", *Molecular Endocrinology*, Vol. 11, pp. 779-791 (1997)). The present CARLA assays use a TR-FRET detection method previously reviewed (see Hemmila, "LANCE: Homogeneous Assay Platform for HTS", *J. Biomol. Screening*, Vol. 4, pp. 303-307 (1999); Mathis, "HTRF Technology", *J. Biomol. Screening*, Vol. 4, pp. 309-313 (1999)). All assays included 3 nM of the glutathione-S-transferase (GST) fusion proteins of either the hPPARα ligand binding domain (LBD) (amino acids 167-468) (GST-hPPARα LBD), GST-hPPARδ LBD (amino acids 139-442) or GST-hPPARγ LBD (amino acids 175-476); 3 nM Eu-labeled anti-GST antibody (Wallac); 30 nM biotinylated steroid receptor coactivator-1 (SRC-1) peptide (an N-terminal biotinylated peptide, CPSSHSSLTERHKILHRLLQEG-SPS, derived from amino acids 676-700 of SRC-1); and 10 nM streptavidin-labelled allophycocyanin (APC; Prozyme). The binding of a ligand to a PPAR LBD alters the conformation of the LBD and permits the biotinylated SRC-1 peptide to bind. This brings the Eu-labeled anti-GST antibody and the strepavidin-labeled APC in close proximity, thereby facilitating fluorescence energy transfer. The biotinylated SRC-1 peptide is prepared by standard solid-phase peptide synthetic methods. The GST-PPAR LBDs are expressed in pGEX vectors (Amersham Pharmacia) in the *E. coli* strain BL21(DE3) using standard expression conditions at 18° C. In some cases the GST-PPAR LBDs are co-expressed with groESL. The GST fusion proteins are purified on glutathione sepharose affinity columns (Amersham Pharmacia) using the method described by the manufacturer. The assay buffer contained 50 mM Tris pH 7.4, 50 mM KCl, 0.1% BSA and 1 mM DTT (dithiothreitol). The assay is carried out in black half area 96-well plates in a final volume of 25 μL. After mixing all components, the reaction mixture stands for 3 hours at room temperature before reading the TR-FRET (Time-Resolved Fluorescence Resonance Energy Transfer) signal on a Wallac Victor 2 plate reader (measuring the ratio of signals at 665 nM and 620 nM). $EC_{50}$ values are estimated with the Excel add-in program XLFit (ID Business Solutions, Guildford, Surrey, UK) utilizing a 4-parameter logistic equation.

The glucose and insulin lowering activity in vivo can be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1, tail blood samples are taken at 8:00 am and plasma glucose levels are determined. The animals are randomly assigned to the control and compound groups. The means of plasma glucose values of the groups were matched. Animals are then orally dosed with vehicle (0.5% carboxymethyl-cellulose with 0.2% Tween-80) or compounds (at 30 mg/kg) in vehicle. The mice are dosed daily for a total of 3 days. On day 4, basal blood samples are taken. The plasma samples are analyzed for glucose concentrations using a YSI2700 Dual Channel Biochemistry Analyzer (Yellow Springs Instrument Co., Yellow Springs, Ohio) and insulin concentrations using an ELISA assay.

Illustrative of the invention, the compound of Example 1 demonstrates an $EC_{50}$ of about 5 nM in the PPARα receptor binding assay, and an $EC_{50}$ of about 3 nM in the PPARγ receptor binding assay.

The following Examples are intended to illustrate the invention and are not to be construed as being limitations thereon. Temperatures are given in degrees Centigrade. If not mentioned otherwise, all evaporations are performed under reduced pressure, preferably between about 5 and 50 mmHg (=20-133 mbar). The structure of final products, intermediates and starting materials is confirmed by standard analytical methods, e.g., microanalysis and spectroscopic characteristics, e.g., MS, IR and NMR. In general, abbreviations used are those conventional in the art.

EXAMPLE 1

1-Ethyl-3-{4-[5-methyl-2-(4-trifluoromethyl-phenyl) oxazol-4-ylmethoxy]-benzene-sulfonylamino}-1H-pyrazole-4-carboxylic acid ethyl ester

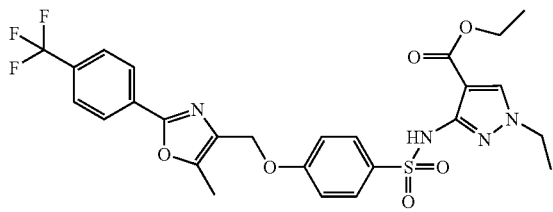

A. 4-Hydroxybenzenesulfonic acid disodium salt

A solution of 4-hydroxybenzenesulfonic acid sodium salt dihydrate (20 g, 86 mmol) in 1 N aqueous sodium hydroxide (86 mL, 86 mmol) is stirred and heated at 50-60° C. for 1 h. The solution is concentrated in vacuo at 50° C. to give a solid. The solid is suspended in anhydrous toluene and concentrated in vacuo. This process is repeated twice. The solid is dried at 50° C. at high vacuum for 18 h to give 4-hydroxybenzenesulfonic acid disodium salt.

B. 4-[5-Methyl-2-(4-trifluoromethyl-phenyl)-oxazol-4-ylmethoxy]-benzenesulfonic acid sodium salt A mixture of the title A compound, 4-hydroxybenzenesulfonic acid disodium salt (0.72 g, 3.3 mmol) and 4-chloromethyl-5-methyl-2-(4-trifluoromethyl-phenyl)-oxazole (1.0 g, 3.63 mmol) in 5 mL of DMF is stirred and heated under nitrogen at 110° C. for 16 h. The cooled reaction mixture is filtered and the solid obtained is washed thoroughly with DCM. The solid is dried overnight to give 4-(5-methyl-2-(4-trifluoromethyl-phenyl)-oxazol-4-ylmethoxy)-benzenesulfonic acid sodium salt: MS [m/z] 412.79 [M-1]⁻.

C. 4-[5-Methyl-2-(4-trifluoromethyl-phenyl)-oxazol-4-ylmethoxy]-benzenesulfonic acid chloride To a solution of thionyl chloride (3.0 mL) and 2 drops of DMF stirring under nitrogen at 0° C. is added the title B compound, 4-(5-methyl-2-(4-trifluoromethyl-phenyl)-oxazol-4-ylmethoxy)-benzenesulfonic acid sodium salt (1.1 g, 2.53 mmol) in one portion. The resulting suspension is stirred at 0° C. for 10 min. The ice bath is removed and the suspension is stirred at RT for 3 h. The solution is concentrated and the resulting residue is azeotrophed twice with toluene. The residue is taken up into DCM, filtered and evaporated at reduced pressure to give 4-[5-methyl-2-(4-trifluoromethyl-phenyl)-oxazol-4-ylmethoxy]-benzenesulfonic acid chloride as an oil. It is used as such without any additional purification.

D. 3-Amino-1-ethyl-1H-pyrazole-4-carboxylic acid ethyl ester

To a solution of 3-amino-1H-pyrazole-4-carboxylic acid ethyl ester (5.0 g, 32 mmol) in acetonitrile is added sodium hydride (1.28 g, 32 mmol) at RT. After 30 min of stirring, a solution of ethyl iodide (2.57 ml, 32 mmol) in acetonitriloe is added dropwise. The reaction mixture is stirred at RT for 16 h. Water is added followed by anhydrous sodium sulfate. The mixture is filtered and concentrated at reduced pressure. The crude product is chromatographed on silica gel using 30% ethyl acetate in hexanes to provide a regioisomeric mixture of N-ethylated 3-amino-1H-pyrazole-4-carboxylic acid ethyl esters. This mixture is used in the following reaction step without further purification.

E. 1-Ethyl-3-{4-[5-methyl-2-(4-trifluoromethyl-phenyl)-oxazol-4-ylmethoxy]-benzenesulfonylamino}-1H-pyrazole-4-carboxylic acid ethyl ester To a solution of the title D compound, a regioisomeric mixture of N-ethylated 3-amino-1H-pyrazole-4-carboxylic acid ethyl esters (0.38 g, 2.1 mmol) and TEA (0.42 g, 4.2 mmol) in DCM at RT, is added dropwise the title C compound, 4-[5-methyl-2-(4-trifluoromethyl-phenyl)oxazol-4-ylmethoxy]-benzenesulfonic acid chloride (0.9 g, 2.1 mmol) in DCM. The solution is stirred at RT 16 h. The reaction mixture is diluted with ethyl acetate, washed with saturated sodium bicarbonate and brine, dried over anhydrous magnesium sulfate, filtered and concentrated at reduced pressure. The crude product is chromatographed on silica gel using 40% ethyl acetate in hexanes to yield 1-ethyl-3-{4-[5-methyl-2-(4-trifluoromethyl-phenyl)-oxazol-4-ylmethoxy]-benzenesulfonylamino}-1H-pyrazole-4-carboxylic acid ethyl ester as white solid: MS [m/z] 577.3 [M-1]⁻.

EXAMPLE 2

1-Ethyl-3-[4-(5-methyl-2-phenyl-oxazol-4-yl-methoxy)-benzenesulfonylamino]-1H-pyrazole-4-carboxylic acid ethyl ester

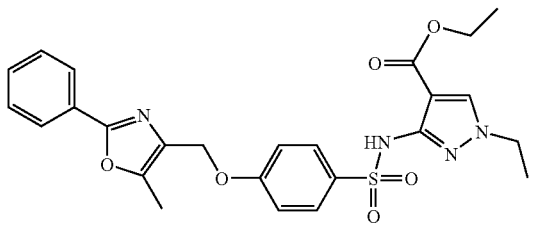

The title compound is prepared analogously to Example 1: MS [m/z] 509.3 [M-1]$^{-1}$.

EXAMPLE 3

1-Ethyl-3-[4-(5-methyl-2-phenyl-oxazol-4-yl-methoxy)-benzenesulfonylamino]-1H-pyrazole-4-carboxylic acid

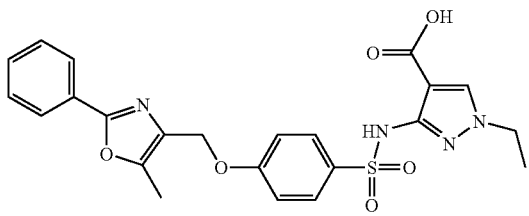

To a solution of the title compound of Example 2, 1-ethyl-3-{4-[5-methyl-2-phenyl-oxazol-4-ylmethoxy]-benzene-sulfonylamino}-1H-pyrazole-4-carboxylic acid ethyl ester (0.09 g, 0.18 mmol) in dioxane (4 mL) is added 2N sodium hydroxide (4 mL) at RT. The reaction mixture is stirred for 4 days. The reaction mixture is acidified with ice-cold 2 N hydrochloric acid (HCl) and placed in an ice bath for 1 h. The solid formed is separated, washed with water and dried under vacuum. The product, 1-ethyl-3-{4-[5-methyl-2-phenyl-oxazol-4-ylmethoxy]-benzenesulfonylamino}-1H-pyrazole-4-carboxylic acid is obtained as a white solid: MS [m/z] 481.1 [M-1]$^-$.

EXAMPLE 4

1-Ethyl-3-[4-(5-methyl-2-phenyl-oxazol-4-yl-methoxy)-benzenesulfonylamino]-1H-pyrazole-4-carboxylic acid amide

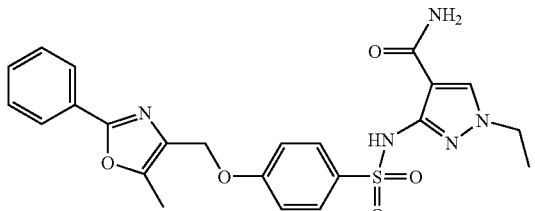

A. 1-Ethyl-3-{4-[5-methyl-2-phenyl-oxazol-4-yl-methoxy]-benzenesulfonylamino}-1H-pyrazole-4-carbonyl chloride To a solution of thionyl chloride (2.0 mL) and 2 drops of DMF in DCM stirring under nitrogen at RT is added the title compound of Example 3, 1-ethyl-3-{4-[5-methyl-2-phenyl-oxazol-4-ylmethoxy]-benzenesulfonylamino}-1H-pyrazole-4-carboxylic acid (0.8 g, 1.65 mmol) in one portion. The resulting suspension is stirred for 16 h. The solution is concentrated and the resulting residue is azeotrophed twice with toluene. It is used as such without any additional purification.

B. 1-Ethyl-3-{4-[5-methyl-2-phenyl-oxazol-4-yl-methoxy]-benzenesulfonylamino}-1H-pyrazole-4-carboxylic acid amide To a solution of the title A compound, 1-ethyl-3-{4-[5-methyl-2-phenyl-oxazol-4-ylmethoxy]-benzenesulfonylamino}-1H-pyrazole-4-carbonyl chloride (0.15 g, 0.3 mmol) in DCM is added a saturated solution of ammonia (3 mL) in DCM at RT. The reaction mixture is stirred for 16 h. The reaction mixture is diluted with ethyl acetate, washed with water, dried and evaporated to give 1-ethyl-3-{4-[5-methyl-2-phenyl-oxazol-4-ylmethoxy]-benzene-sulfonylamino}-1H-pyrazole-4-carboxylic acid amide as a solid: MS [m/z] 481.5 [M-1]$^-$.

EXAMPLE 5

1-Ethyl-3-{4-[5-methyl-2-phenyl-oxazol-4-yl-methoxy]-benzenesulfonylamino}-1H-pyrazole-4-carboxylic acid ethyl amide

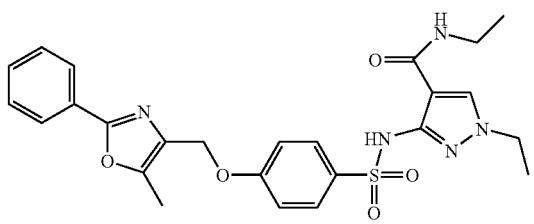

To a solution of the title compound of Example 3 (0.15 g, 0.31 mmol), EDCl (0.12 g, 0.62 mmol), 1-hydroxybenzotriazole (0.42 g, 0.31 mmol) and TEA (0.2 g, 1.5 mmol) in DCM, is added ethylamine hydrochloride (0.5 g, 0.62 mmol) at RT. The reaction mixture is stirred for 16 h. The reaction mixture is diluted with ethyl acetate, washed with 1N hydrochloric acid, water and brine. The organic filtrate is concentrated, the crude is chromatographed using 25% ethyl acetate in hexanes to provide 1-ethyl-3-{4-[5-methyl-2-phenyl-oxazol-4-yl-methoxy]-benzenesulfonylamino}-1H-pyrazole-4-carboxylic acid ethyl amide as a crystalline solid: MS [m/z] 508.1 [M-1]$^-$.

EXAMPLE 6

N-(4-Benzoyl-1-ethyl-1H-pyrazol-3-yl)-4-(5-methyl-2-phenyl-oxazol-4-ylmethoxy)-benzenesulfonamide

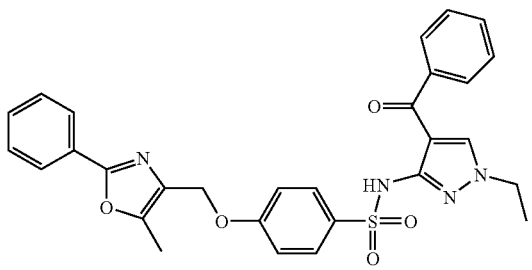

A. (3-Amino-1-ethyl-1H-pyrazol-4-yl)-phenyl-methanone

To a vigorously stirring solution of (3-amino-1H-pyrazol-4-yl)-phenyl-methanone (0.1 g, 0.53 mmol) in dry DMF at RT is added sodium hydride (0.023 g, 0.57 mmol). After 1 h, ethyl iodide (0.042 mL, 0.53 mmol) is added and stirring is continued for 4 h. The reaction mixture is diluted with ethyl acetate, washed with water, brine and dried over anhydrous sodium sulfate. The organic filtrate is concentrated and the crude is chromatographed on silica gel using 50% ethyl acetate in hexanes to provide (3-amino-1-ethyl-1H-pyrazol-4-yl)-phenyl-methanone.

B. N-(4-Benzoyl-1-ethyl-1H-pyrazol-3-yl)-4-(5-methyl-2-phenyl-oxazol-4-ylmethoxy)-benzenesulfonamide To a solution of the title A compound, (3-amino-1-ethyl-1H-pyrazol-4-yl)-phenyl-methanone (0.035 g, 0.16 mmol) in pyridine at RT, is added 4-(5-methyl-2-phenyl-oxazol-4-ylmethoxy)-benzenesulfonyl chloride (0.06 g, 0.16 mmol) in pyridine. The solution is stirred at RT for 16 h. The reaction mixture is concentrated, the residue is taken up into ethyl acetate, washed with 1 N HCl, water, saturated sodium bicarbonate and brine, dried over anhydrous magnesium sulfate, filtered and concentrated at reduced pressure. The crude product is chromatographed on silica gel using 50% ethyl acetate in hexanes to yield N-(4-benzoyl-1-ethyl-1H-pyrazol-3-yl)-4-(5-methyl-2-phenyl-oxazol-4-ylmethoxy)-benzenesulfonamide as a solid: MS [m/z] 541.1 [M-1]⁻.

EXAMPLE 7

The following compounds are prepared analogously to the previous Examples.

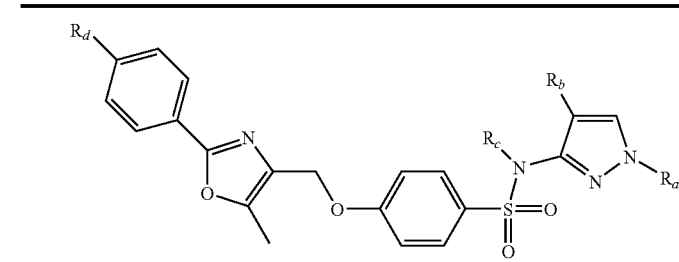

| Example | $R_a$ | $R_b$ | $R_c$ | $R_d$ | MS [m/z] |
|---|---|---|---|---|---|
| 7-1 | H | —COOH | H | H | 453.8 [M −1]⁻ |
| 7-2 | PhCH₂— | —COOEt | H | H | 571.1 [M − 1]⁻ |
| 7-3 | PhCH₂— | —COOH | H | H | 543.1 [M − 1]⁻ |
| 7-4 | Me | —COOEt | H | H | 495.0 [M − 1]⁻ |
| 7-5 | Me | —COOH | H | H | 467.2 [M − 1]⁻ |
| 7-6 | H₂C=CH—CH₂— | —COOEt | H | H | 521.1 [M − 1]⁻ |
| 7-7 | H₂C=CH—CH₂— | —COOH | H | H | 493.2 [M − 1]⁻ |
| 7-8 | Ph | —COOEt | H | —CF₃ | 625.6 [M − 1]⁻ |
| 7-9 | n-Pr | —COOEt | H | H | 523.3 [M − 1]⁻ |
| 7-10 | Et | —CONHMe | H | H | 494.3 [M − 1]⁻ |
| 7-11 | Et | —CONMe₂ | H | H | 508.3 [M − 1]⁻ |
| 7-12 | Et | —CONHCH₂-c-Pr[a] | H | H | 534.3 [M − 1]⁻ |
| 7-13 | Et | —CONHCH₂Ph | H | H | 570.2 [M − 1]⁻ |
| 7-14 | Et | —CON(piperidinyl) | H | H | 548.2 [M − 1]⁻ |
| 7-15 | Et | —COOEt | Me | H | 525.0 [M − 1]⁻ |

[a] c-Pr refers to a cyclopropyl group

What is claimed is:

1. A compound of the formula

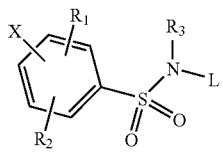

(I)

wherein
R₁ and R₂ are independently hydrogen, halogen, hydroxy, optionally substituted alkyl, alkoxy, alkylthio, aralkyl or heteroaralkyl; or
R₁ and R₂ combined together with the carbon atoms to which they are attached form an optionally substituted fused 5- to 6-membered aromatic or heteroaromatic ring provided that R₁ and R₂ are attached to carbon atoms adjacent to each other; or
R₁ and R₂ combined are alkylene which together with the carbon atoms to which they are attached form a fused 5- to 7-membered ring provided that R₁ and R₂ are attached to carbon atoms adjacent to each other; or
R₃ is hydrogen or optionally substituted lower alkyl;
X is -Z-(CH₂)$_p$-Q-W wherein
Z is O, S, S(O), or S(O)₂; or
p is an integer from 1 to 8;
Q is a bond;

W is

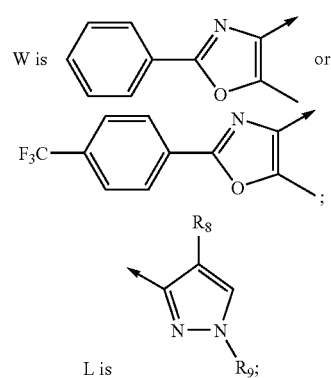

L is

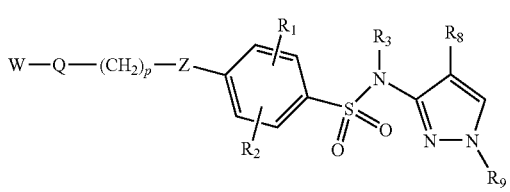

R₈ is optionally substituted alkyl, aralkyl, alkoxy, alkylthio, —C(O)R₁₀, —C(O)OR₁₁ or —C(O)NR₁₂R₁₃ in which
R₁₀ is optionally substituted lower alkyl;
R₁₁, R₁₂ and R₁₃ are independently hydrogen or optionally substituted lower alkyl;
R₉ is hydrogen, optionally substituted alkyl, aryl or aralkyl;
or a pharmaceutically acceptable salt thereof.

2. A compound according to claim 1 of the formula (IB)

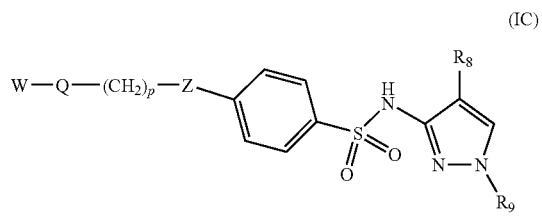

wherein
R₁ and R₂ are independently hydrogen, halogen, hydroxy, optionally substituted alkyl, alkoxy, alkylthio, aralkyl or heteroaralkyl;
R₃ is hydrogen;
O, S, S(O), or S(O)₂;
p is an integer from 1 to 5;
Q is a bond;
W is

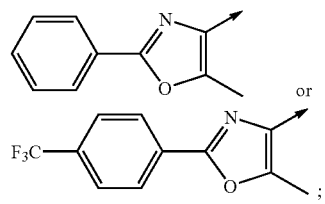

R₈ is optionally substituted alkyl, aralkyl, alkoxy, alkylthio, —C(O)R₁₀, —C(O)OR₁₁ or —C(O)NR₁₂R₁₃ in which
R₁₀ is optionally substituted lower alkyl;
R₁₁, R₁₂ and R₁₃ are independently hydrogen or optionally substituted lower alkyl;
R₉ is hydrogen, optionally substituted alkyl, aryl or aralkyl;
or a pharmaceutically acceptable salt thereof; or a prodrug derivative thereof.

3. A compound according to claim 2, wherein
R₁ and R₂ are hydrogen;
or a pharmaceutically acceptable salt thereof; or a prodrug derivative thereof.

4. A compound according to claim 3 of the formula (IC)

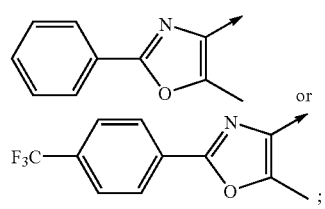

wherein
Z is O or S;
p is an integer from 1 to 5;
Q is a bond;
W is

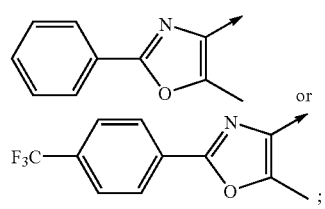

R₈ is optionally substituted alkyl, aralkyl, alkoxy, alkylthio, —C(O)R₁₀, —C(O)OR₁₁ or —C(O)NR₁₂R₁₃ in which
R₁₀ is optionally substituted lower alkyl;
R₁₁, R₁₂ and R₁₃ are independently hydrogen or optionally substituted lower alkyl;

R₉ is hydrogen, optionally substituted alkyl, aryl or aralkyl; or a pharmaceutically acceptable salt thereof; or a prodrug derivative thereof.

5. A compound according to claim 4, wherein
R₈ is —C(O)OR₁₁ in which R₁₁ is hydrogen or lower alkyl;
R₉ is lower alkyl;
or a pharmaceutically acceptable salt thereof; or a prodrug derivative thereof.

6. A compound according to claim 5, wherein
R₈ is —C(O)OR₁₁ in which R₁₁ is ethyl;
R₉ is ethyl;
or a pharmaceutically acceptable salt thereof.

7. A compound according to claim 5, wherein
Z is O or S;
p is an integer of 1 or 2;
Q is a bond;
W is

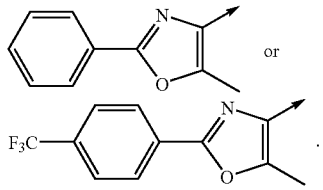

8. A compound according to claim 1, which is selected from the group consisting of:

3-[4-(5-Methyl-2-phenyl-oxazol-4-ylmethoxy)-benzene-sulfonylamino]-1H-pyrazole-4-carboxylic acid;

1-Benzyl-3-[4-(5-methyl-2-phenyl-oxazol-4-ylmethoxy)-benzenesulfonylamino]-1H-pyrazole-4-carboxylic acid ethyl ester;

1-Benzyl-3-[4-(5-methyl-2-phenyl-oxazol-4-ylmethoxy)-benzenesulfonylamino]-1H-pyrazole-4-carboxylic acid;

1-Methyl-3-[4-(5-methyl-2-phenyl-oxazol-4-ylmethoxy)-benzenesulfonylamino]-1H-pyrazole-4-carboxylic acid ethyl ester;

1-Methyl-3-[4-(5-methyl-2-phenyl-oxazol-4-ylmethoxy)-benzenesulfonylamino]-1H-pyrazole-4-carboxylic acid;

1-Ethyl-3-[4-(5-methyl-2-phenyl-oxazol-4-ylmethoxy)-benzenesulfonylamino]-1H-pyrazole-4-carboxylic acid ethyl ester;

1-Ethyl-3-[4-(5-methyl-2-phenyl-oxazol-4-ylmethoxy)-benzenesulfonylamino]-1H-pyrazole-4-carboxylic acid;

1-Allyl-3-[4-(5-methyl-2-phenyl-oxazol-4-ylmethoxy)-benzenesulfonylamino]-1H-pyrazole-4-carboxylic acid ethyl ester;

1-Ally-3-[4-(5-methyl-2-phenyl-oxazol-4-ylmethoxy)-benzenesulfonylamino]-1H-pyrazole-4-carboxylic acid;

3-{4-[5-Methyl-2-(4-trifluoromethyl-phenyl)-oxazol-4-ylmethoxy]-benzene-sulfonylamino}-1-phenyl-1H-pyrazole-4-carboxylic acid ethyl ester;

3-[4-(5-Methyl-2-phenyl-oxazol-4-ylmethoxy)-benzene-sulfonylamino]-1-propyl-1H-pyrazole-4-carboxylic acid ethyl ester;

1-Ethyl-3-{4-[5-methyl-2-(4-trifluoromethyl-phenyl)-oxazol-4-ylmethoxy]-benzene-sulfonylamino}-1H-pyrazole-4-carboxylic acid ethyl ester;

1-Ethyl-3-[4-(5-methyl-2-phenyl-oxazol-4-ylmethoxy)-benzenesulfonylamino]-1H-pyrazole-4-carboxylic acid methylamide;

1-Ethyl-3-[4-(5-methyl-2-phenyl-oxazol-4-ylmethoxy)-benzenesulfonylamino]-H-pyrazole-4-carboxylic acid dimethylamide;

1-Ethyl-3-[4-(5-methyl-2-phenyl-oxazol-4-ylmethoxy)-benzenesulfonylamino]-H-pyrazole-4-carboxylic acid cyclopropylmethyl-amide;

1-Ethyl-3-[4-(5-methyl-2-phenyl-oxazol-4-ylmethoxy)-benzenesulfonylamino]-1H-pyrazole-4-carboxylic acid amide;

1-Ethyl-3-[4-(5-methyl-2-phenyl-oxazol-4-ylmethoxy)-benzenesulfonylamino]-1H-pyrazole-4-carboxylic acid ethylamide;

1-Ethyl-3-[4-(5-methyl-2-phenyl-oxazol-4-ylmethoxy)-benzenesulfonylamino]-1H-pyrazole-4-carboxylic acid benzylamide;

N-[1-Ethyl-4-(piperidine-1-carbonyl)-1H-pyrazol-3-yl]-4-(5-methyl-2-phenyl-oxazol-4-ylmethoxy)-benzene-sulfonamide;

N-(4-Benzoyl-1-ethyl-1H-pyrazol-3-yl)-4-(5-methyl-2-phenyl-oxazol-4-ylmethoxy)-benzenesulfonamide; and 1-Ethyl-3-{methyl-[4-(5-methyl-2-phenyl-oxazol-4-ylmethoxy)-benzenesulfonyl]-amino}-1H-pyrazole-4-carboxylic acid ethyl ester;

or a pharmaceutically acceptable salt thereof.

9. A pharmaceutical composition comprising a therapeutically effective amount of a compound of claim 1 in combination with one or more pharmaceutically acceptable carriers.

10. A pharmaceutical composition comprising a therapeutically effective amount of a compound of claim 1 in combination with a therapeutically effective amount of insulin, insulin derivative or mimetic; insulin secretagogue; insulinotropic sulfonylurea receptor ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid; or aspirin.

* * * * *